US012758604B2

(12) United States Patent
Sun et al.

(10) Patent No.: US 12,758,604 B2
(45) Date of Patent: Oct. 13, 2026

(54) PHARMACEUTICAL COMPOSITION FOR TREATING MYOCARDIAL ISCHEMIA AND PREPARATION METHOD THEREFOR

(71) Applicant: TASLY PHARMACEUTICAL GROUP CO., LTD., Tianjin (CN)

(72) Inventors: He Sun, Tianjin (CN); Kaijing Yan, Tianjin (CN); Xiaohui Ma, Tianjin (CN); Shunnan Zhang, Tianjin (CN); Yi He, Tianjin (CN); Haoshu Xiong, Tianjin (CN); Yongfeng Zheng, Tianjin (CN); Xinxin Li, Tianjin (CN); Hongbo Zhang, Tianjin (CN); Yanmei Li, Tianjin (CN); Jing Wang, Tianjin (CN); Tiantian Wen, Tianjin (CN); Zhipeng Huo, Tianjin (CN); Lijun Fan, Tianjin (CN); Wei Sun, Tianjin (CN); Jianchun Wang, Tianjin (CN); Nan Cai, Tianjin (CN); Rui Yang, Tianjin (CN); Jingjing Zhang, Tianjin (CN)

(73) Assignee: TASLY PHARMACEUTICAL GROUP CO., LTD., Tianjin (CN)

( * ) Notice: Subject to any disclaimer, the term of this patent is extended or adjusted under 35 U.S.C. 154(b) by 680 days.

(21) Appl. No.: 18/034,362

(22) PCT Filed: Sep. 5, 2022

(86) PCT No.: PCT/CN2022/116975

§ 371 (c)(1),
(2) Date: Apr. 27, 2023

(87) PCT Pub. No.: WO2023/045740

PCT Pub. Date: Mar. 30, 2023

(65) Prior Publication Data

US 2023/0390353 A1 Dec. 7, 2023

(30) Foreign Application Priority Data

Sep. 27, 2021 (CN) .......................... 202111136641.6

(51) Int. Cl.

| | |
|---|---|
| *A61K 36/537* | (2006.01) |
| *A61K 31/045* | (2006.01) |
| *A61K 31/495* | (2006.01) |
| *A61K 36/258* | (2006.01) |
| *A61P 9/10* | (2006.01) |

(52) U.S. Cl.
CPC .......... *A61K 36/537* (2013.01); *A61K 31/045* (2013.01); *A61K 31/495* (2013.01); *A61K 36/258* (2013.01); *A61P 9/10* (2018.01)

(58) Field of Classification Search
CPC .................................................... A61K 36/537
See application file for complete search history.

(56) References Cited

U.S. PATENT DOCUMENTS

| | | | | |
|---|---|---|---|---|
| 5,506,229 A | | 4/1996 | Dow et al. | |
| 2009/0111826 A1 | * | 4/2009 | Lange | A61K 31/495 514/252.12 |

FOREIGN PATENT DOCUMENTS

| | | | | | |
|---|---|---|---|---|---|
| CN | 1421239 A | * | 6/2003 | | |
| CN | 100998648 A | | 7/2007 | | |
| CN | 104274520 A | | 1/2015 | | |
| CN | 110898024 A | | 3/2020 | | |
| CN | 111297942 A | * | 6/2020 | ................ | A61P 9/10 |

OTHER PUBLICATIONS

International Patent Application No. PCT/CN2022/116975; Int'l Search Report; dated Nov. 25, 2022; 3 pages.
Du Han-Cheng; "Effects of Ranolazine Combined with Xueshuantong Capsule on Cell Autophagy and Myocardial NF-kB, p-Akt, IP7 Levels During Myocardial Ischemia-reperfusion Injury in Diabetic Rats"; China Journal of Pharmaceutical Economics; vol. 15 No. 9; 2020; p. 39-43 (contains English Abstract).

* cited by examiner

*Primary Examiner* — Gina C Justice
(74) *Attorney, Agent, or Firm* — BakerHostetler

(57) ABSTRACT

The present invention provides a pharmaceutical composition for treating myocardial ischemia, comprising Salvia Miltiorrhiza medicinal material 250-700 parts by weight, Radix Notoginseng medicinal material 50-150 parts by weight, Borneolum Syntheticum 3-9 parts by weight, and ranolazine 25-100 parts by weight. According to a further aspect of the present invention, there is provided a use of a pharmaceutical composition for preparation of a medicine for prevention and/or treatment of myocardial ischemia.

12 Claims, No Drawings

PHARMACEUTICAL COMPOSITION FOR TREATING MYOCARDIAL ISCHEMIA AND PREPARATION METHOD THEREFOR

CROSS-REFERENCE TO RELATED APPLICATIONS

This application is the U.S. National Stage of International Application No. PCT/CN2022/116975, filed on Sep. 5, 2022, which claims priority to Chinese Patent Application No. 202111136641.6, filed on Sep. 27, 2021, the entire contents of both of which are incorporated herein by reference.

TECHNICAL FIELD

The present invention relates to the field of traditional Chinese medicine preparation, especially to a pharmaceutical composition for treating myocardial ischemia, a preparation method thereof and an application in the preparation of a medicine for prevention and/or treatment of myocardial ischemia.

BACKGROUND ART

Ranolazine, with the chemical name (±)-N-(2,6-dimethylphenyl)-4-[2-hydroxy-3-(2-methoxyphenoxy) propyl]-1-piperazine acetamide, has the structural formula shown in the following figure:

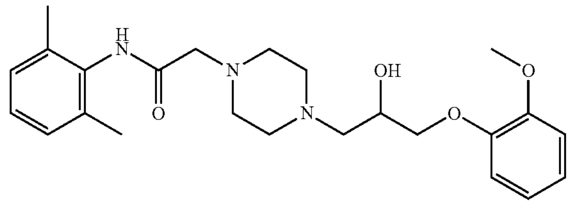 [SMILES: COc1ccccc1OCC(O)CN1CCN(CC(=O)Nc2c(C)cccc2C)CC1]

It is used for treatment of chronic stable angina pectoris. It has anti-angina pectoris and anti-myocardial ischemia functions, and its specific mechanism is not clear. Ranolazine is limited to patients who are refractory to antianginal medications such as long-acting nitrates, calcium channel blockers, and beta-2 receptor blockers. Clinical trials have shown that male patients take ranolazine with better effects than female patients.

Salvia miltiorrhiza is also known as Radix salviae miltiorrhizae, HONGGEN, etc. It is the root and rhizome of Salvia miltiorrhiza Bge. Salvia miltiorrhiza has the effects of activating blood circulation and dispelling blood stasis, cooling blood and eliminating carbuncle, and nourishing blood to tranquillize the mind. It can dilate coronary artery and increase coronary blood flow, and has significant protective effect on myocardial ischemia, which is beneficial to the prevention and treatment of coronary disease and angina pectoris. It can improve the body's microcirculation, reduce blood viscosity, and reduce platelet aggregation.

Radix Notoginseng is also named Kaihua Radix Notoginseng, panax pseudoginseng, pseudo-ginseng, GINBUHUAN, PANLONGQI. Radix Notoginseng has effects of dissipating blood stasis to stop bleeding, reducing swelling and relieving pain. It mainly treats hemoptysis, hematemesis, epistaxis, hematochezia, metrorrhagia, traumatic hemorrhage, thorax and abdominal stabbing pain, and tumescent pain.

Borneolum Syntheticum is also known as borneol, Ju Pian, Ai Pian, Dipterocarp, etc. Its chemical composition is 2-camphanol, and the chemical formula is $C_{10}H_{18}O$. It has the effects of inducing reuscitation and refreshing spirit, clearing heat and removing toxic substances, and improving eyesight and removing nebula. It mainly treats calentura and unconsciousness due to high fever, apoplexy, syncope due to accumulation of phlegm, and convulsion, affecting upper orifices by heat-damp in summer, sore throat and deafness, aphtha and tooth swelling, carbuncle sore and hemorrhoid, conjunctival congestion and swelling pain, and pterygium.

Chinese patent application CN111297942A discloses a compound preparation for treating myocardial ischemia including ranolazine and a mixture consisting of Salvia miltiorrhiza, Radix Notoginseng and Borneolum Syntheticum. Herein, the parts by weight of each component are as follows: ranolazine 20-50 parts, a mixture consisting of Salvia miltiorrhiza, Radix Notoginseng, and Borneolum Syntheticum 20-50 parts. The method for preparing the compound preparation includes the following steps:

step 1, weighing each component separately and sieving the same for later use;

step 2, dissolving the binder in water for later use;

step 3, putting all the components, except the lubricant, into a wet-type granulator, premixing the same, adding an aqueous binder solution, and then adding water; after the granulation is completed, transferring the same to a fluidized bed for drying, and sieving and granulating;

step 4, adding the granulated materials into a mixer, adding the lubricant and mixing well to prepare an intermediate; and step 5, filling the intermediate into capsules or compressed into tablets or prepared as granules.

However, the application does not specifically disclose the ratio among Salvia miltiorrhiza, Radix Notoginseng and Borneolum Syntheticum, thus rendering the technical solution of the application unclear and unfeasible. In addition, it can be seen according to the embodiments of the patent application that the amount of ranolazine used is higher than that of a mixture composed of Salvia miltiorrhiza, Radix Notoginseng and Borneolum Syntheticum (Embodiment 1: ranolazine 250 g, and a mixture 125 g consisting of Salvia miltiorrhiza, Radix Notoginseng and Borneolum Syntheticum; Embodiment 2: ranolazine 275 g, and a mixture 100 g of Salvia miltiorrhiza, Radix Notoginseng and Borneolum Syntheticum; Embodiment 3: ranolazine 300 g, and a mixture 75 g of Salvia miltiorrhiza, Radix Notoginseng and Borneolum Syntheticum).

SUMMARY OF THE INVENTION

Based on the prior art, the present invention studies the dosage of Salvia miltiorrhiza, Radix Notoginseng, Borneolum Syntheticum and ranolazine to provide a new pharmaceutical composition for treating myocardial ischemia. The pharmaceutical composition of the present invention can reduce the dosage of ranolazine under the premise of preventing and/or treating myocardial ischemia, thereby alleviating some toxic and side effects possibly existing in chemical drugs.

The pharmaceutical composition of the present invention comprises Salvia miltiorrhiza medicinal material 250-700 parts by weight, Radix Notoginseng medicinal material 50-150 parts by weight, Borneolum Syntheticum 3-9 parts by weight, and ranolazine 25-100 parts by weight.

According to the pharmaceutical composition of the present invention, the Salvia miltiorrhiza medicinal material and the Radix Notoginseng medicinal material are extracted to obtain a Salvia miltiorrhiza and Radix Notoginseng extract or directly pulverized and mixed to obtain a Salvia miltiorrhiza and Radix Notoginseng mixture.

In an embodiment, according to the pharmaceutical composition, the Salvia miltiorrhiza medicinal material and the Radix Notoginseng medicinal material are performed with merged extraction as follows: Salvia miltiorrhiza and Radix Notoginseng are decocted together with water in an alkaline condition, the decocting solution is filtered, and the filtrate is concentrated and precipitated with alcohol; the supernatant is filtered, and alcohol is recovered to obtain an extractum, that is the Salvia miltiorrhiza and Radix Notoginseng extract, or the extractum is dried to obtain the Salvia miltiorrhiza and Radix Notoginseng extract.

Preferably, the Salvia miltiorrhiza medicinal material and the Radix Notoginseng medicinal material are performed with merged extraction as follows:

step (1), Salvia miltiorrhiza and Radix Notoginseng are decocted with water in an alkaline condition for 1-3 times and for 1-3 hours each time, and the mixture is filtered to obtain a filtrate I for later use;

step (2), medicinal residues are decocted with added water for 1-3 times and 1-3 hours each time, and the mixture is filtered to obtain a filtrate II for later use;

step (3), the filtrates I and II are merged and concentrated, and the concentrate is precipitated with alcohol, leaving standstill; the supernatant is filtered, alcohol is recovered, and the solution is concentrated to obtain an extractum, that is the Salvia miltiorrhiza and Radix Notoginseng extract, or the extractum is dried to obtain the Salvia miltiorrhiza and Radix Notoginseng extract.

The alkaline conditions described in the step (1) are not limited to one or more of sodium bicarbonate, sodium carbonate, sodium hydrogen phosphate, sodium dihydrogen phosphate, sodium hydroxide, potassium hydroxide and magnesium hydroxide, at the pH of 7.5-9.0, with the amount added being 1-4.5% (preferably 2.25-3%) of the medicinal material.

In the step (3), it is preferably for precipitation by adding 70-100% ethanol (optimally, 95% ethanol), preferably to a concentration of 60-75% by the ethanol precipitation.

Most preferably, the Salvia miltiorrhiza and Radix Notoginseng extract of the present invention is prepared by the following method:

step (1): the Salvia miltiorrhiza medicinal material is cut to 5 cm or less, the Radix Notoginseng is pulverized into particles with a diameter of 1 cm or less for later use; an appropriate amount of sodium bicarbonate is weighed (2.25-3% of the amount of medicinal materials) for later use; the weighed Salvia miltiorrhiza, Radix Notoginseng and sodium bicarbonate are put into an extraction tank; 5 times amount of process water is added into each tank, and then heated and boiled. Keep boiling for about 2 h±20 min, and the mixture is filtered;

step (2), a second extraction is performed on medicinal residues, 4 times the amount of water is added, the mixture is heated and boiled. Keep boiling for about 1 h±15 min, filtered, and the medicinal residues are discarded;

step (3), the extracting solution is concentrated under reduced pressure to a relative density of 1.16-1.20 (80±5° C.) or a corresponding sugar degree of 48-52% to obtain a concentrate; the concentrate is put into an ethanol precipitation tank, an appropriate amount of ethanol is added to adjust the ethanol content to 65-70%, standing for 12-24 hours until the precipitation is complete; the supernatant is separated and the precipitate is discarded; the supernatant is concentrated to obtain an extractum, that is the Salvia miltiorrhiza and Radix Notoginseng extract, or the extractum is dried to obtain the Salvia miltiorrhiza and Radix Notoginseng extract.

In the second embodiment, according to the pharmaceutical composition of the present invention, the Salvia miltiorrhiza medicinal material and the Radix Notoginseng medicinal material are respectively extracted by water extraction and alcohol precipitation under alkaline conditions, and the obtained Salvia miltiorrhiza extract and Radix Notoginseng extract are mixed to obtain the Salvia miltiorrhiza and Radix Notoginseng extract.

Preferably, the Salvia miltiorrhiza is decocted with water for 1-3 times under alkaline conditions, decocted for 1-3 hours each time, filtered; the filtrates are merged and concentrated, the concentrate is precipitated with alcohol, and allowed to stand; the supernatant is filtered, alcohol is recovered, and concentrated to obtain an extractum, that is a Salvia miltiorrhiza extract, or the extractum is dried to obtain a Salvia miltiorrhiza extract.

Under alkaline conditions, Radix Notoginseng is decocted with water for 1-3 times, decocted for 1-3 hours each time, and filtered; the filtrates are merged and concentrated, the concentrate is precipitated with alcohol, and allowed to stand; the supernatant is filtered, alcohol is recovered, and the solution is concentrated to obtain an extractum, that is a Radix Notoginseng extract, or the extractum is dried to obtain a Radix Notoginseng extract.

The Salvia miltiorrhiza extract is merged with the Radix Notoginseng extract to obtain the Salvia miltiorrhiza and Radix Notoginseng extract.

Most preferably, for the Salvia miltiorrhiza extract, firstly, Salvia miltiorrhiza is added into an extraction tank, and then an appropriate amount of sodium bicarbonate (2.25% of the amount of medicinal material) is added into the extraction tank, 5 times of water is added into the extraction tank, and the mixture is decocted at 100° C. for 2 hours and filtered; the medicinal residues are extracted for the second time, added with 4 times amount of water, decocted at 100° C. for 1 hour, filtered, and the medicinal residues are discarded. The two decocting filtrates are merged and concentrated under reduced pressure at 80° C.-90° C. to a relative density of 1.16-1.20 (80±1° C.) or a sugar degree of 48%-52% to obtain a concentrate; an appropriate amount of ethanol is added to the concentrate to adjust the ethanol content to 65%-70% (20° C.), leaving standing at low temperature for 12 hours-24 hours until the precipitation is complete; the supernatant is separated, and the precipitate is discarded; and the supernatant is concentrated under reduced pressure to 82%-88% sugar degree to obtain the Salvia miltiorrhiza extract.

Radix Notoginseng extract: the Radix Notoginseng is pulverized into particles with a diameter of 1.5 cm or less; the extraction tank is firstly charged with pulverized Radix Notoginseng, added with 5 times of water, and soaked for 12-15 hours, then added with an appropriate amount of sodium bicarbonate (2.25% of the amount of medicinal materials), decocted at 100° C. for 2 hours, and filtered; the medicinal residues are extracted for the second time, added with 4 times amount of water, decocted at 100° C. for 1 hour, filtered, and the medicinal residues are discarded. The two decocting filtrates are merged, and concentrated under reduced pressure at 80° C.-90° C. to a sugar degree of 18%-28% to obtain a concentrate; an appropriate amount of ethanol is added to the concentrate to adjust the ethanol content to 65%-70% (20° C.), leaving standing at low temperature for 15 hours-24 hours until the precipitation is complete; the supernatant is separated, and the precipitate is discarded; the supernatant is concentrated under reduced pressure to 60%-75% sugar degree, so as to obtain a Radix Notoginseng extract.

The Salvia miltiorrhiza extract is merged with the Radix Notoginseng extract to obtain the Salvia miltiorrhiza and Radix Notoginseng extract.

In the third embodiment, according to the pharmaceutical composition of the present invention, the Salvia miltiorrhiza medicinal material and the Radix Notoginseng medicinal material are performed with merged extraction as follows: Salvia miltiorrhiza and Radix Notoginseng are extracted with alcohol and then water, the extract is filtered, and the filtrate is concentrated to obtain an extractum, that is the Salvia miltiorrhiza and Radix Notoginseng extract, or the extractum is dried to obtain the Salvia miltiorrhiza and Radix Notoginseng extract.

Preferably, the Salvia miltiorrhiza medicinal material and the Radix Notoginseng medicinal material are performed with merged extraction as follows:

- step (1), Salvia miltiorrhiza and Radix Notoginseng are extracted with ethanol for 1-3 times and 1-3 hours each time, and the mixture is filtered to obtain a filtrate I for later use;
- step (2), medicinal residues are decocted with added water for 1-3 times and 1-3 hours each time, and the mixture is filtered to obtain a filtrate II for later use;
- step (3), the filtrate II is firstly concentrated, and then the filtrate I is added for concentration to obtain an extractum, that is the Salvia miltiorrhiza and Radix Notoginseng extract, or the extractum is dried to obtain the Salvia miltiorrhiza and Radix Notoginseng extract.

In the step (1), 70-100% ethanol extraction (optimally, 90% ethanol) is preferably performed.

Most preferably, the Salvia miltiorrhiza and Radix Notoginseng extract of the present invention is prepared by the following method:

- step (1), the Salvia miltiorrhiza medicinal material is cut to 5 cm or less, the Radix Notoginseng is pulverized into particles with a diameter of 1 cm or less for later use; the weighed Salvia miltiorrhiza and Radix Notoginseng are put into an extraction tank, 4 times amount of 90% ethanol is added into each tank, and the mixture is heated and boiled. Keep boiling about 90 min±20 min, and filtered;
- step (2), water extraction is performed on the medicine residues, 5 times the amount of water is added, the mixture is heated and boiled. Keep boiling at about 60 min±15 min, and filtered; and the medicine residues are discarded;
- step (3), the water extracting solution is concentrated under reduced pressure to a relative density of 1.25-1.30 (82±5° C.), and the ethanol extract is gradually added and the mixture is further concentrated to obtain an extractum, that is the Salvia miltiorrhiza and Radix Notoginseng extract, or the extractum is dried to obtain the Salvia miltiorrhiza and Radix Notoginseng extract.

In the fourth embodiment, according to the pharmaceutical composition of the present invention, the Salvia miltiorrhiza medicinal material is extracted with alcohol and then water to obtain an extractum, and the Radix Notoginseng medicinal material is pulverized and then mixed with the above extractum to obtain the Salvia miltiorrhiza and Radix Notoginseng extract.

Preferably, the Salvia miltiorrhiza and Radix Notoginseng of the present invention are extracted and pulverized as follows:

- step (1), Salvia miltiorrhiza is extracted with ethanol for 1-3 times and 1-3 hours each time, and the mixture is filtered to obtain a filtrate I for later use;
- step (2), medicinal residues are decocted with added water for 1-3 times, 1-3 hours each time, and the mixture is filtered to obtain a filtrate II for later use;
- step (3), the filtrate II is first concentrated, and then the filtrate I is added for concentration to obtain an extractum;
- step (4), Radix Notoginseng is pulverized and sieved by a Pharmacopoeia No. 5 sieve to obtain fine powder;
- step (5), the fine powder of Radix Notoginseng is added to the extractum obtained in step (3), and the mixture is mixed uniformly to obtain a Salvia miltiorrhiza and Radix Notoginseng extract, or the extractum is dried to obtain the Salvia miltiorrhiza and Radix Notoginseng extract.

In the step (1), 70-100% ethanol extraction (optimally, 90% ethanol) is preferably performed. Most preferably, the Salvia miltiorrhiza and Radix Notoginseng extract of the present invention is prepared by the following method:

- step (1), the Salvia miltiorrhiza medicinal material is cut to 5 cm or less; the weighed Salvia miltiorrhiza is put into an extraction tank, 4 times amount of 90% ethanol is added into each tank, and the mixture is heated and boiled. Keep boiling about 90 min±20 min, and filtered;
- step (2), water extraction is performed on the medicine residues, 5 times the amount of water is added, the mixture is heated and boiled. Keep boiling at about 60 min±15 min, and filtered; and the medicine residues are discarded;
- step (3), the water extracting solution is concentrated under reduced pressure to a relative density of 1.25-1.30 (82±5° C.), and the ethanol extract is gradually added and the mixture is further concentrated to obtain an extractum;
- step (4), the Radix Notoginseng medicinal material is pulverized and sieved by a Pharmacopoeia No. 5 sieve to obtain fine powder;
- step (5), the fine powder of Radix Notoginseng is added to the extractum obtained in step (3), and the mixture is mixed uniformly to obtain a Salvia miltiorrhiza and Radix Notoginseng extract, or the extractum is dried to obtain the Salvia miltiorrhiza and Radix Notoginseng extract.

In the fifth embodiment, according to the pharmaceutical composition of the present invention, the Salvia miltiorrhiza medicinal material and the Radix Notoginseng medicinal material can also be pulverized respectively and then mixed to obtain the Salvia miltiorrhiza and Radix Notoginseng mixture.

In an embodiment, the Salvia miltiorrhiza and Radix Notoginseng extract or mixture of the present invention can be further mixed with Borneolum Syntheticum and excipients to prepare an intermediate 1; the ranolazine and excipients are mixed to obtain an intermediate 2; and the intermediates are loaded in different layers, and then the corresponding preparation is prepared. Specifically, the corresponding preparation is bi-layer tablet, bi-layer drop pill, bi-layer pellet or the like. For example, in certain embodiments, one of the intermediate 1 and the intermediate 2, as described above, may be formulated as a pill core having medicine, a tablet core, a drop pill, and another as a drug-containing coating, thereby forming a bi-layer tablet, a bi-layer drop pill, a bi-layer pellet, etc.

In another embodiment, the Salvia miltiorrhiza and Radix Notoginseng extract or mixture of the present invention can also be further mixed with Borneolum Syntheticum and excipients to prepare a corresponding preparation, and the ranolazine is mixed with the excipients to prepare a corresponding preparation, the two preparations are combined and packaged together.

The combination and packaged together means that the two preparations are mixed and filled into a suitable preparation, or the two preparations are mixed and bagged and packaged into a divided-dose package.

The corresponding preparation can be any suitable preparation form.

Preferred preparations include tablets, capsules, granules, drop pills, pills, oral liquid, powder, sublimed preparation, ointments, emulsion, transdermal preparation, or inhalation preparation and the like.

The tablets include common tablets, micro-tablets, etc.; the capsules include hard capsules, soft capsules and the like; the drop pills include common drop pills and micro-drop pills; and the pellet include common pills and pellets.

More preferred preparations include drop pills, pills, tablets, and capsules.

Preferably, the excipients of the present invention may contain commonly used excipients such as binders, fillers, diluents, tableting agents, lubricants, disintegrants, coloring agents, flavoring agents and wetting agents, and may be coated if necessary.

Suitable fillers include microcrystalline cellulose, mannitol, lactose and other similar fillers.

Suitable disintegrants include starch, crospolyvinylpyrrolidone, croscarmellose sodium and starch derivatives such as sodium starch glycolate.

Suitable lubricants include, for example, magnesium stearate.

Suitable pharmaceutically acceptable wetting agents include sodium lauryl sulfate.

Solid oral compositions may be prepared by conventional methods of blending, filling, tableting and the like. Repeated mixing can be carried out to distribute the active substance throughout those compositions employing large amounts of fillers.

The preparation of the present invention is most preferably a common pill or a micro-drop pill.

The common drop pills or micro-drop pills of the present invention are prepared by mixing a pharmaceutically active ingredient (e.g., a pharmaceutical composition of the present invention, or Salvia Miltiorrhiza and Radix Notoginseng extract, or the mixture of Salvia Miltiorrhiza and Radix Notoginseng extract and Borneolum Syntheticum, or ranolazine) with a drop pill base in a weight ratio of 1:5 to 5:1.

Preferably, the common drop pills or micro-drop pills of the present invention are prepared from the pharmaceutically active ingredient and the drop pill base in a weight ratio of 1:3 to 3:1.

Most preferably, it is composed of the pharmaceutically active ingredient and the dropping pill base in a weight ratio of 1:1-3.

The drop pill base is selected from one of polyethylene glycol, sorbitol, xylitol, lactitol, erythritol, poloxamer 188, polyvinylpyrrolidone, stearic acid, maltose, starch, methyl cellulose, sodium carboxymethyl cellulose, hydroxypropylmethyl cellulose, gum arabic, gelatin, alginic acid, dextrin, cyclodextrin, agar, and lactose. Preferably, polyethylene glycols includes such as solid polyethylene glycols 1000-8000, that is, a combination of one or more of polyethylene glycols 1000, 2000, 3000, 4000, 6000, 8000, most preferably polyethylene glycol 6000 or 4000 or a polyethylene glycol 4000-6000 combination.

The preparation method of the common drop pill or micro-drop pill according to the present invention is provided by the prior art, for example, the method disclosed in Chinese patent CN104274520 A or CN 104274518 A.

The invention further provides a use of a pharmaceutical composition for preparation of a medicine for prevention and/or treatment of myocardial ischemia.

The pharmaceutical composition of the present invention is superior to the prior art (e.g., a Chinese traditional medicine consisting of Salvia Miltiorrhiza, Radix Notoginseng and Borneolum Syntheticum, or ranolazine used alone) in the prevention and/or treatment of myocardial ischemia. The pharmaceutical composition of the present invention can reduce the amount of ranolazine and greatly reduce the toxic side effects that may exist when the ranolazine is used alone while ensuring the therapeutic effect.

DETAILED DESCRIPTION OF THE INVENTION

Embodiment 1

1, The pharmaceutical composition of the present invention is composed of Salvia Miltiorrhiza medicinal material 1250 mg, Radix Notoginseng medicinal material 250 mg, Borneolum Syntheticum 15 mg, ranolazine 500 mg.

2, Salvia miltiorrhiza and Radix Notoginseng extract is prepared as follows:

step (1): the Salvia miltiorrhiza medicinal material is cut to 5 cm or less, the Radix Notoginseng is pulverized into particles with a diameter of 1 cm or less for later use; an appropriate amount of sodium bicarbonate is weighed (2.25-3% of the amount of medicinal materials) for later use; the weighed Salvia miltiorrhiza, Radix Notoginseng and sodium bicarbonate are put into an extraction tank; 5 times amount of process water is added into each tank, heated and boiled. Keep boiling for about 2 h±20 min, and the mixture is filtered;

step (2), a second extraction is performed on medicinal residues, 4 times the amount of water is added, the mixture is heated and boiled. Keep boiling for about 1 h±15 min, filtered, and the medicinal residues are discarded;

step (3), the extracting solution is concentrated under reduced pressure to a relative density of 1.16-1.20 (80±5° C.) or a corresponding sugar degree of 48-52% to obtain a concentrate; the concentrate is put into an ethanol precipitation tank, an appropriate amount of ethanol is added to adjust the ethanol content to 65-70%, standing for 12-24 hours until the precipitation is complete; the supernatant is separated and the precipitate is discarded; and the supernatant is concentrated to obtain a Salvia miltiorrhiza and Radix Notoginseng extract, and the solid content (the amount of water removed, i.e., the dried weight) thereof is about 150 mg.

3, The Salvia miltiorrhiza and Radix Notoginseng extract of the present invention, Borneolum Syntheticum and excipients are prepared as a micro-drop pill preparation according to the following method:

| | |
|---|---|
| Salvia miltiorrhiza and Radix Notoginseng extract (dried weight) | 150 mg |
| Borneolum Syntheticum | 15 mg |
| Polyethylene glycol 6000 | 220 mg |
| Polyethylene glycol 4000 | 110 mg |

After mixing polyethylene glycol 4000 and polyethylene glycol 6000, the mixture is heated and melted, added with Borneolum Syntheticum, Salvia miltiorrhiza and Radix Notoginseng extract, and an appropriate amount of purified water, thoroughly mixed and homogenized, and performed with shaking and dripping, condensing, drying, coating and screening to obtain micro-drop pills.

4, Ranolazine micro-drop pills of the present invention are prepared according to the following formulation:

| | |
|---|---|
| Ranolazine | 500 mg |
| Polyethylene glycol 6000 | 199 mg |
| Polyethylene glycol 4000 | 796 mg |
| Sodium lauryl sulfate | 5 mg |

After mixing polyethylene glycol 4000 and polyethylene glycol 6000, the mixture is heated and melted, added with ranolazine fine powder and sodium lauryl sulfate, mixed thoroughly and homogenized, and performed with dropping, condensing and screening to obtain ranolazine micro-drop pills.

5, The above-mentioned micro-drop pills and ranolazine micro-drop pills are mixed well and filled into No. 0 gelatin capsules to obtain a pharmaceutical composition preparation of the present invention.

Embodiment 2

1, The pharmaceutical composition of the present invention is composed of Salvia Miltiorrhiza medicinal material 7000 mg, Radix Notoginseng medicinal material 1500 mg, Borneolum Syntheticum 45 mg, ranolazine 500 mg.

2, Salvia miltiorrhiza and Radix Notoginseng extract is prepared as follows:

step (1): the Salvia miltiorrhiza medicinal material is cut to 5 cm or less, the Radix Notoginseng is pulverized into particles with a diameter of 1 cm or less for later use; an appropriate amount of sodium bicarbonate is weighed (2.25-3% of the amount of medicinal materials) for later use; the weighed Salvia miltiorrhiza, Radix Notoginseng and sodium bicarbonate are put into an extraction tank; 5 times amount of process water is added into each tank, heated and boiled. Keep boiling for about 2 h±20 min, and the mixture is filtered;

step (2), a second extraction is performed on medicinal residues, 4 times the amount of water is added, the mixture is heated and boiled. Keep boiling for about 1 h±15 min, filtered, and the medicinal residues are discarded;

step (3), the extracting solution is concentrated under reduced pressure to a relative density of 1.16-1.20 (80±5° C.) or a corresponding sugar degree of 48-52% to obtain a concentrate; the concentrate is put into an ethanol precipitation tank, an appropriate amount of ethanol is added to adjust the ethanol content to 65-70%, standing for 12-24 hours until the precipitation is complete; the supernatant is separated and the precipitate is discarded; and the supernatant is concentrated to obtain a Salvia miltiorrhiza and Radix Notoginseng extract, and the solid content (the amount of water removed, i.e., the dried weight) thereof is about 450 mg.

3, The Salvia miltiorrhiza and Radix Notoginseng extract of the present invention, Borneolum Syntheticum and excipients are prepared as a micro-drop pill preparation according to the following method:

| | |
|---|---|
| Salvia miltiorrhiza and Radix Notoginseng extract (dried weight) | 450 mg |
| Borneolum Syntheticum | 45 mg |
| Poloxamer 188 | 90 mg |
| Polyethylene glycol 6000 | 900 mg |

After mixing polyethylene glycol 6000 and poloxamer 188, the mixture is heated and melted, added with Borneolum Syntheticum, Salvia miltiorrhiza and Radix Notoginseng extract, and an appropriate amount of purified water, thoroughly mixed and homogenized, and performed with shaking and dripping, condensing, drying, coating and screening to obtain micro-drop pills.

4, Ranolazine micro-drop pills are prepared according to the following formulation:

| | |
|---|---|
| Ranolazine | 500 mg |
| Polyethylene glycol 3350 | 500 mg |
| Polyethylene glycol 4000 | 495 mg |
| Tween 80 | 5 mg |

After mixing polyethylene glycol 4000 and polyethylene glycol 3350, the mixture is heated and melted, added with ranolazine fine powder and Tween 80, mixed thoroughly and homogenized, and performed with dropping, condensing and screening to obtain ranolazine micro-drop pills. 5, The above-mentioned micro-drop pills and ranolazine micro-drop pills are mixed uniformly and loaded into a pharmaceutical aluminum-plastic composite film bag to obtain a pharmaceutical composition preparation of the present invention.

Embodiment 3

1, The pharmaceutical composition of the present invention is composed of Salvia Miltiorrhiza medicinal material 7000 mg, Radix Notoginseng medicinal material 1500 mg, Borneolum Syntheticum 45 mg, ranolazine 250 mg.

2, Salvia miltiorrhiza and Radix Notoginseng extract is prepared as follows:

step (1): the Salvia miltiorrhiza medicinal material is cut to 5 cm or less, the Radix Notoginseng is pulverized into particles with a diameter of 1 cm or less for later use; an appropriate amount of sodium bicarbonate is weighed (2.25-3% of the amount of medicinal materials) for later use; the weighed Salvia miltiorrhiza, Radix Notoginseng and sodium bicarbonate are put into an extraction tank; 5 times amount of process water is added into each tank, heated and boiled. Keep boiling for about 2 h±20 min, and the mixture is filtered;

step (2), a second extraction is performed on medicinal residues, 4 times the amount of water is added, the mixture is heated and boiled. Keep boiling for about 1 h±15 min, filtered, and the medicinal residues are discarded;

step (3), the extracting solution is concentrated under reduced pressure to a relative density of 1.16-1.20

(80±5° C.) or a corresponding sugar degree of 48-52% to obtain a concentrate; the concentrate is put into an ethanol precipitation tank, an appropriate amount of ethanol is added to adjust the ethanol content to 65-70%, standing for 12-24 hours until the precipitation is complete; the supernatant is separated and the precipitate is discarded; and the supernatant is concentrated to obtain a Salvia miltiorrhiza and Radix Notoginseng extract, and the solid content (the amount of water removed, i.e., the dried weight) thereof is about 450 mg.

3, The Salvia miltiorrhiza and Radix Notoginseng extract of the present invention, Borneolum Syntheticum and excipients are prepared as a micro-drop pill preparation according to the following method:

| | |
|---|---|
| Salvia miltiorrhiza and Radix Notoginseng extract (dried weight) | 450 mg |
| Borneolum Syntheticum | 45 mg |
| Polyethylene glycol 6000 | 990 mg |

Polyethylene glycol 6000 is heated and melted, added with Borneolum Syntheticum, Salvia miltiorrhiza and Radix Notoginseng extract, and an appropriate amount of purified water, thoroughly mixed and homogenized, and performed with shaking and dripping, condensing, drying, coating and screening to obtain micro-drop pills.

4, Ranolazine micro-tablets are prepared according to the following formulation:

| | |
|---|---|
| Ranolazine | 250 mg |
| Lactose | 200 mg |
| Low-substituted hydroxypropyl cellulose | 20 mg |
| Polyethylene glycol 6000 | 20 mg |
| Sodium lauryl sulfate | 2 mg |
| Micropowder silica gel | 3 mg |
| Magnesium stearate | 5 mg |

The ranolazine fine powder is mixed with lactose, low-substituted hydroxypropyl cellulose, polyethylene glycol 6000 and sodium lauryl sulfate to prepare granules, the granules are thoroughly mixed with micro-powder silica gel and magnesium stearate, and the mixture is pressed for micro-tablets to obtain ranolazine micro-tablets.

5, The above-mentioned micro-drop pills and ranolazine micro-tablets are sequentially loaded into No. 0 gelatin capsules to obtain a pharmaceutical composition preparation of the present invention.

Embodiment 4

1, The pharmaceutical composition of the present invention is composed of Salvia Miltiorrhiza medicinal material 1250 mg, Radix Notoginseng medicinal material 250 mg, Borneolum Syntheticum 15 mg, and ranolazine 250 mg.

2, Salvia miltiorrhiza and Radix Notoginseng extract is prepared as follows:

step (1), the Salvia miltiorrhiza medicinal material is cut to 5 cm or less, the Radix Notoginseng is pulverized into particles with a diameter of 1 cm or less for later use; an appropriate amount of sodium bicarbonate is weighed (2.25-3% of the amount of medicinal materials) for later use; the weighed Salvia miltiorrhiza, Radix Notoginseng and sodium bicarbonate are put into an extraction tank; 4 times amount of process water is added into each tank, heated and boiled. Keep boiling for about 3 h, and the mixture is filtered;

step (2), a second extraction is performed on medicinal residues, 5 times the amount of water is added, the mixture is heated and boiled. Keep boiling for about 2 h, filtered, and the medicinal residues are discarded;

step (3), the extracting solution is concentrated under reduced pressure to a relative density of 1.16-1.20 (80±5° C.) or a corresponding sugar degree of 48-52% to obtain a concentrate; the concentrate is put into an ethanol precipitation tank, an appropriate amount of ethanol is added to adjust the ethanol content to 65-70%, standing for 12-24 hours until the precipitation is complete; the supernatant is separated and the precipitate is discarded; and the supernatant is concentrated to obtain a Salvia miltiorrhiza and Radix Notoginseng extract, and the solid content (the amount of water removed, i.e., the dried weight) thereof is about 150 mg.

3, The Salvia miltiorrhiza and Radix Notoginseng extract of the present invention, Borneolum Syntheticum and excipients are prepared as a micro-drop pill preparation according to the following method:

| | |
|---|---|
| Salvia miltiorrhiza and Radix Notoginseng extract (dried weight) | 150 mg |
| Borneolum Syntheticum | 15 mg |
| Polyvinylpyrrolidone | 30 mg |
| Polyethylene glycol 6000 | 300 mg |

After mixing polyethylene glycol 6000 and polyvinyl pyrrolidone, the mixture is heated and melted, added with Borneolum Syntheticum, Salvia miltiorrhiza and Radix Notoginseng extract, and an appropriate amount of purified water, thoroughly mixed and homogenized, and performed with shaking and dripping, condensing, drying, coating and screening to obtain micro-drop pills.

4, Ranolazine micro-tablets are prepared according to the following formulation:

| | |
|---|---|
| Ranolazine | 250 mg |
| Microcrystalline cellulose | 300 mg |
| Pregelatinized starch | 50 mg |
| Crospovidone | 24 mg |
| Starch slurry | 11 mg |
| Span 20 | 2 mg |
| Magnesium stearate | 3 mg |

The ranolazine fine powder is mixed with microcrystalline cellulose, pregelatinized starch and crospovidone uniformly. The mixture of starch slurry and Span 20 is added as a binder to the above-mentioned mixed powder for granulation and drying. After sieving, the above resultant is added with magnesium stearate and mixed uniformly, and compressed to obtain ranolazine micro-tablets.

5, The above-mentioned micro-drop pills are loaded into No. 0 gelatin capsules, and ranolazine micro-tablets are loaded into No. 0 gelatin capsules, and the two capsules are bubbling-packed side by side to obtain the pharmaceutical composition preparation of the present invention.

Embodiment 5

1, The pharmaceutical composition of the present invention is composed of Salvia Miltiorrhiza medicinal material 2500 mg, Radix Notoginseng medicinal material 500 mg, Borneolum Syntheticum 60 mg, ranolazine 1000 mg.

2, Salvia miltiorrhiza and Radix Notoginseng extract is prepared as follows:

Salvia miltiorrhiza extract: firstly, Salvia miltiorrhiza is added into an extraction tank, and then an appropriate amount of sodium bicarbonate (2.25% of the amount of medicinal material) is added into the extraction tank, 5 times of water is added into the extraction tank, and the mixture is decocted at 100° C. for 3 hours and filtered; the medicinal residues are extracted for the second time, added with 5 times amount of water, decocted at 100° C. for 2 hours, filtered, and the medicinal residues are discarded. The two decocting filtrates are merged and concentrated under reduced pressure at 80° C.-90° C. to a relative density of 1.16-1.20 (80±1° C.) or a sugar degree of 48%-52% to obtain a concentrate; an appropriate amount of ethanol is added to the concentrate to adjust the ethanol content to 65%-70% (20° C.), leaving standing at low temperature for 12 hours-24 hours until the precipitation is complete; the supernatant is separated, and the precipitate is discarded; and the supernatant is concentrated under reduced pressure to 82%-88% sugar degree to obtain a Salvia miltiorrhiza extract.

Radix Notoginseng extract: the Radix Notoginseng is pulverized into particles with a diameter of 1.5 cm or less; the extraction tank is firstly charged with pulverized Radix Notoginseng, added with 5 times of water, and soaked for 12-15 hours, then added with an appropriate amount of sodium bicarbonate (2.25% of the amount of medicinal materials), decocted at 100° C. for 3 hours, and filtered; the medicinal residues are extracted for the second time, added with 5 times amount of water, decocted at 100° C. for 2 hours, filtered, and the medicinal residues are discarded. The two decocting filtrates are merged, and concentrated under reduced pressure at 80° C.-90° C. to a sugar degree of 18%-28% to obtain a concentrate; an appropriate amount of ethanol is added to the concentrate to adjust the ethanol content to 65%-70% (20° C.), leaving standing at low temperature for 15 hours-24 hours until the precipitation is complete; the supernatant is separated, and the precipitate is discarded; the supernatant is concentrated under reduced pressure to 60%-75% sugar degree, so as to obtain a Radix Notoginseng extract.

The Salvia miltiorrhiza extract is merged with the Radix Notoginseng extract to obtain the Salvia miltiorrhiza and Radix Notoginseng extract. The solid content (the amount of water removed, i.e., the dried weight) is about 200 mg.

3, The Salvia miltiorrhiza and Radix Notoginseng extract of the present invention, Borneolum Syntheticum and excipients are prepared as a micro-drop pill preparation according to the following method:

| | |
|---|---|
| Salvia miltiorrhiza and Radix Notoginseng extract (dried weight) | 200 mg |
| Borneolum Syntheticum | 60 mg |
| Polyethylene glycol 6000 | 600 mg |

After polyethylene glycol 6000 is heated and melted, it is added with Borneolum Syntheticum, Salvia miltiorrhiza and Radix Notoginseng extract, and an appropriate amount of purified water, thoroughly mixed and homogenized, and performed with shaking and dripping, condensing, drying, coating and screening to obtain micro-drop pills, and load the micro-drop pills into No. 0 capsules.

4, Ranolazine tablets are prepared according to the following formulation:

| | |
|---|---|
| Ranolazine | 1000 mg |
| Microcrystalline cellulose | 284 mg |
| Methacrylic acid copolymer type C | 400 mg |
| Polyvinylpyrrolidone | 40 mg |
| Methyl methacrylate/ethyl acrylate 30% aqueous dispersion (dry basis) | 200 mg |
| Sodium hydroxide | 16 mg |
| Croscarmellose sodium | 40 mg |
| Magnesium stearate | 20 mg |

Ranolazine fine powder is mixed with methacrylic acid copolymer type C, microcrystalline cellulose and polyvinylpyrrolidone uniformly; sodium hydroxide aqueous solution is added as a binder into the above-mentioned mixed powder to prepare granules; a 30% aqueous dispersion of methyl methacrylate/ethyl acrylate is added into wet granules; the obtained granules are dried, and after sieving, added with croscarmellose sodium and magnesium stearate, mixed uniformly, and compressed to obtain ranolazine sustained-release tablets.

5, Ranolazine sustained-release tablets and micro-drop pill capsules are bubbling-packed in one row to obtain the pharmaceutical composition formulation of the present invention.

Embodiment 6

1, The pharmaceutical composition of the present invention is composed of Salvia Miltiorrhiza medicinal material 2500 mg, Radix Notoginseng medicinal material 1500 mg, Borneolum Syntheticum 60 mg, and ranolazine 375 mg.

2, Salvia miltiorrhiza and Radix Notoginseng extract is prepared as follows:

Salvia miltiorrhiza extract: firstly, Salvia miltiorrhiza is added into an extraction tank, and then an appropriate amount of sodium bicarbonate (2.25% of the amount of medicinal material) is added into the extraction tank, 5 times of water is added into the extraction tank, and the mixture is decocted at 100° C. for 2 hours and filtered; the medicinal residues are extracted for the second time, added with 4 times amount of water, decocted at 100° C. for 1 hour, filtered, and the medicinal residues are discarded. The two decocting filtrates are merged and concentrated under reduced pressure at 80° C.-90° C. to a relative density of 1.16-1.20 (80±1° C.) or a sugar degree of 48%-52% to obtain a concentrate; an appropriate amount of ethanol is added to the concentrate to adjust the ethanol content to 65%-70% (20° C.), leaving standing at low temperature for 12 hours-24 hours until the precipitation is complete; the supernatant is separated, and the precipitate is discarded; and the supernatant is concentrated under reduced pressure to 82%-88% sugar degree to obtain a Salvia miltiorrhiza extract.

Radix Notoginseng extract: the Radix Notoginseng is pulverized into particles with a diameter of 1.5 cm or less; the extraction tank is firstly charged with pulverized Radix Notoginseng, added with 5 times of water, and soaked for 12-15 hours, then added with an appropriate amount of sodium bicarbonate (2.25% of the amount of medicinal materials), decocted at 100° C. for 2 hours, and filtered; the medicinal residues are extracted for the second time, added with 4 times amount of water, decocted at 100° C. for 1 hour, filtered, and the medicinal residues are discarded. The two decocting filtrates are merged, and concentrated under reduced pressure at 80° C.-90° C. to a sugar degree of 18%-28% to obtain a concentrate; an appropriate amount of ethanol is added to the concentrate to adjust the ethanol content to 65%-70% (20° C.), leaving standing at low temperature for 15 hours-24 hours until the precipitation is complete; the supernatant is separated, and the precipitate is discarded; the supernatant is concentrated under reduced pressure to 60%-75% sugar degree, so as to obtain a Radix Notoginseng extract.

The Salvia miltiorrhiza extract is merged with the Radix Notoginseng extract to obtain the Salvia miltiorrhiza and Radix Notoginseng extract. The solid content (the amount of water removed, i.e., the dried weight) is about 300 mg.

3, The Salvia miltiorrhiza and Radix Notoginseng extract of the present invention, Borneolum Syntheticum and excipients are prepared as a micro-drop pill preparation according to the following method:

| | |
|---|---|
| Salvia miltiorrhiza and Radix Notoginseng extract (dried weight) | 300 mg |
| Borneolum Syntheticum | 60 mg |
| Gelatin | 50 mg |
| Polyethylene glycol 4000 | 750 mg |

After mixing polyethylene glycol 4000 and gelatin, the mixture is heated and melted, added with Borneolum Syntheticum, the Salvia miltiorrhiza and Radix Notoginseng extract, and an appropriate amount of purified water, thoroughly mixed and homogenized, and performed with shaking and dripping, condensing, drying, coating and screening to obtain micro-drop pills.

4, Ranolazine sustained release micro-tablets are prepared according to the following formulation:

| | |
|---|---|
| Ranolazine | 375 mg |
| Microcrystalline cellulose | 53 mg |
| Methacrylic acid copolymer type C | 50 mg |
| Sodium hydroxide | 2 mg |
| Hypromellose | 10 mg |
| Magnesium stearate | 10 mg |

The ranolazine fine powder is mixed with methacrylic acid copolymer type C, microcrystalline cellulose and hypromellose uniformly; the mixture is added with aqueous sodium hydroxide solution, performed with granulating, drying, and sieving, added with magnesium stearate and mixed uniformly, and then compressed and coated to obtain sustained-release ranolazine micro-tablets.

5, The ranolazine sustained-release micro-tablets and micro-drop pills described above are sequentially loaded into No. 0 gelatin capsules to provide a pharmaceutical composition formulation of the present invention.

Embodiment 7

1, The pharmaceutical composition of the present invention is composed of Salvia Miltiorrhiza medicinal material 1250 mg, Radix Notoginseng medicinal material 250 mg, Borneolum Syntheticum 45 mg, and ranolazine 250 mg.

2, Salvia miltiorrhiza and Radix Notoginseng mixture is prepared as follows:

Salvia miltiorrhiza is pulverized and screened by an 80 mesh sieve.

Radix Notoginseng is pulverized and screened by an 80 mesh sieve.

The above-mentioned powders are mixed to obtain a Salvia miltiorrhiza and Radix Notoginseng mixture.

3, The Salvia miltiorrhiza and Radix Notoginseng mixture of the present invention is mixed with Borneolum Syntheticum and micropowder silica gel to obtain a mixed powder:

| | |
|---|---|
| Salvia miltiorrhiza and Radix Notoginseng mixture | 1500 mg |
| Borneolum Syntheticum | 45 mg |
| Micropowder silica gel | 8 mg |

4, Ranolazine micro-tablets are prepared according to the following formulation:

| | |
|---|---|
| Ranolazine | 250 mg |
| Starch | 200 mg |
| Low-substituted hydroxypropyl cellulose | 25 mg |
| Sodium carboxymethyl cellulose | 18 mg |
| Tween 80 | 2 mg |
| Magnesium stearate | 5 mg |

The ranolazine fine powder is mixed with starch, low-substituted hydroxypropyl cellulose, sodium carboxymethyl cellulose and Tween 80 uniformly; the mixture is added with purified water to granulate, dried and granulated, added with magnesium stearate, mixed uniformly and compressed to obtain ranolazine micro-tablets.

5, The above-mentioned ranolazine micro-tablets and the Salvia miltiorrhiza and Radix Notoginseng mixture are mixed into powder and then filled into No. 0 gelatin capsules in order to obtain a pharmaceutical composition preparation of the present invention.

Embodiment 8

1, The pharmaceutical composition of the present invention is composed of Salvia Miltiorrhiza medicinal material 7000 mg, Radix Notoginseng medicinal material 500 mg, Borneolum Syntheticum 45 mg, and ranolazine 250 mg.

2, Salvia miltiorrhiza and Radix Notoginseng extract is prepared as follows:

step (1), the Salvia miltiorrhiza medicinal material is cut to 5 cm or less, the Radix Notoginseng is pulverized into particles with 1 cm or less for later use; an appropriate amount of sodium bicarbonate is weighed (2.25-3% of the amount of medicinal materials) for later use; the weighed Salvia miltiorrhiza, Radix Notoginseng and sodium bicarbonate are put into an extraction tank; 4 times amount of process water is added into each tank, heated and boiled. Keep boiling for about 3 hours, and the mixture is filtered;

step (2), a second extraction is performed on medicinal residues, 5 times the amount of water is added, the mixture is heated and boiled. Keep boiling for about 2 hours, filtered, and the medicinal residues are discarded;

step (3), the extracting solution is concentrated under reduced pressure to a relative density of 1.16-1.20 (80±5° C.) or a corresponding sugar degree of 48-52% to obtain a concentrate; the concentrate is put into an ethanol precipitation tank, an appropriate amount of ethanol is added to adjust the ethanol content to 65-70%, standing for 12-24 hours until the precipitation is complete; the supernatant is separated and the precipitate is discarded; and the supernatant is concentrated to obtain a Salvia miltiorrhiza and Radix Notoginseng extract, and the solid content (the amount of water removed, i.e., the dried weight) thereof is about 450 mg.

3, The Salvia miltiorrhiza and Radix Notoginseng extract of the present invention, Borneolum Syntheticum and excipients are prepared as a micro-drop pill preparation according to the following method:

| | |
|---|---|
| Salvia miltiorrhiza and Radix Notoginseng extract (dried weight) | 450 mg |
| Borneolum Syntheticum | 45 mg |
| Xylitol | 45 mg |
| Erythritol | 90 mg |
| Polyethylene glycol 6000 | 745 mg |

After mixing polyethylene glycol 6000, erythritol and xylitol, the mixture is heated and melted, added with Borneolum Syntheticum, the Salvia miltiorrhiza and Radix Notoginseng extract, and an appropriate amount of purified water, thoroughly mixed and homogenized, and performed with shaking and dripping, condensing, drying, coating and screening to obtain micro-drop pills.

4, Ranolazine pellets are prepared according to the following formulation:

| | |
|---|---|
| Ranolazine | 250 mg |
| Microcrystalline cellulose | 150 mg |
| Sucrose powder | 200 mg |
| Crospovidone | 38 mg |
| Span 20 | 2 mg |

Ranolazine fine powder is mixed with microcrystalline cellulose, sucrose powder and crospovidone uniformly, a soft material is prepared with Span 20 water suspension as a binder, extruded and rounded, dried and sieved to obtain ranolazine pellets.

5, After the above-mentioned micro-drop pills and ranolazine pellets are mixed well, they are loaded into No. 0 gelatin capsules to obtain a pharmaceutical composition preparation.

Embodiment 9

1, The pharmaceutical composition of the present invention is composed of Salvia Miltiorrhiza medicinal material 7000 mg, Radix Notoginseng medicinal material 500 mg, Borneolum Syntheticum 45 mg, and ranolazine 250 mg.

2, Salvia miltiorrhiza and Radix Notoginseng extract is prepared as follows:

step (1), the Salvia miltiorrhiza medicinal material is cut to 5 cm or less, the Radix Notoginseng is pulverized into particles with a diameter of 1 cm or less for later use; an appropriate amount of sodium bicarbonate is weighed (2.25-3% of the amount of medicinal materials) for later use; the weighed Salvia miltiorrhiza, Radix Notoginseng and sodium bicarbonate are put into an extraction tank; 4 times amount of process water is added into each tank, heated and boiled. Keep boiling for about 3 hours, and the mixture is filtered;

step (2), a second extraction is performed on medicinal residues, 5 times the amount of water is added, the mixture is heated and boiled. Keep boiling for about 2 hours, filtered, and the medicinal residues are discarded;

step (3), the extracting solution is concentrated under reduced pressure to a relative density of 1.16-1.20 (80±5° C.) or a corresponding sugar degree of 48-52% to obtain a concentrate; the concentrate is put into an ethanol precipitation tank, an appropriate amount of ethanol is added to adjust the ethanol content to 65-70%, standing for 12-24 hours until the precipitation is complete; the supernatant is separated and the precipitate is discarded; and the supernatant is concentrated to obtain a Salvia miltiorrhiza and Radix Notoginseng extract, and the solid content (the amount of water removed, i.e., the dried weight) thereof is about 450 mg.

3, The outer layer of the bi-layer drop pill of the present invention is a layer of Salvia miltiorrhiza and Radix Notoginseng, and the dropping feed liquid is prepared according to the following method:

| | |
|---|---|
| Salvia miltiorrhiza and Radix Notoginseng extract (dried weight) | 450 mg |
| Borneolum Syntheticum | 45 mg |
| Polyethylene glycol 6000 | 1000 mg |

Polyethylene glycol 6000 is heated and melted, added with Borneolum Syntheticum, Salvia miltiorrhiza and Radix Notoginseng extract, and an appropriate amount of purified water, thoroughly mixed and homogenized to obtain the feed liquid of outer layer.

4, The inner layer of the bi-layer drop pill is a ranolazine layer, and the dropping feed liquid is prepared according to the following formula:

| | |
|---|---|
| Ranolazine | 250 mg |
| Polyethylene glycol 4000 | 750 mg |

The polyethylene glycol 4000 is heated and melted, and the ranolazine fine powder is added and mixed thoroughly to obtain the feed liquid of inner layer.

5, The above-mentioned two feed liquids are made into bi-layer drop pills, and loaded into a pharmaceutical aluminium-plastic composite film bag to obtain a pharmaceutical composition preparation.

Embodiment 10

1, The pharmaceutical composition of the present invention is composed of Salvia Miltiorrhiza medicinal material 1250 mg, Radix Notoginseng medicinal material 250 mg, Borneolum Syntheticum 30 mg, and ranolazine 500 mg.

2, Salvia miltiorrhiza and Radix Notoginseng extract is prepared as follows:

step (1), the Salvia miltiorrhiza medicinal material is cut to 5 cm or less, the Radix Notoginseng is pulverized into particles with 1 cm or less for later use; an appropriate amount of sodium bicarbonate is weighed (2.25-3% of the amount of medicinal materials) for later use; the weighed Salvia miltiorrhiza, Radix Notoginseng and sodium bicarbonate are put into an extraction tank; 4 times amount of process water is added into each tank, heated and boiled. Keep boiling for about 3 hours, and the mixture is filtered;

step (2), a second extraction is performed on medicinal residues, 5 times the amount of water is added, the mixture is heated and boiled. Keep boiling for about 2 hours, filtered, and the medicinal residues are discarded;

step (3), the extracting solution is concentrated under reduced pressure to a relative density of 1.16-1.20 (80±5° C.) or a corresponding sugar degree of 48-52% to obtain a concentrate; the concentrate is put into an ethanol precipitation tank, an appropriate amount of ethanol is added to adjust the ethanol content to 65-70%, standing for 12-24 hours until the precipitation is complete; the supernatant is separated and the precipitate is discarded; and the supernatant is concentrated to obtain a Salvia miltiorrhiza and Radix Notoginseng extract, and the solid content (the amount of water removed, i.e., the dried weight) thereof is about 150 mg.

3, Ranolazine pellets are prepared according to the following formulation:

| | |
|---|---|
| Ranolazine | 500 mg |
| Microcrystalline cellulose | 300 mg |
| Sucrose powder | 400 mg |
| Crospovidone | 80 mg |

Ranolazine fine powder is mixed with microcrystalline cellulose, sucrose powder and crospovidone uniformly, soft material is prepared with water as a binder, extruded and rounded, dried and sieved to obtain ranolazine pellets.

4, The Borneolum Syntheticum fine powder is suspended in the extract of Salvia miltiorrhiza and Radix Notoginseng, mixed well with water, and sprayed onto the ranolazine pellets in a fluidized state to obtain bi-layer pellets; and the pellets are filled into No. 0 gelatin capsules to obtain a pharmaceutical composition preparation.

Embodiment 11

1, The pharmaceutical composition of the present invention is composed of Salvia Miltiorrhiza medicinal material 2500 mg, Radix Notoginseng medicinal material 500 mg, Borneolum Syntheticum 30 mg, and ranolazine 500 mg.

2, Salvia miltiorrhiza and Radix Notoginseng extract is prepared as follows:

step (1), the Salvia miltiorrhiza medicinal material is cut to 5 cm or less; the weighed Salvia miltiorrhiza is put into an extraction tank, 4 times amount of 90% ethanol is added into each tank, and the mixture is heated and boiled. Keep boiling about 90 min, and filtered;

step (2), water extraction is performed on the medicine residues, 5 times the amount of water is added, the mixture is heated and boiled. Keep boiling at about 60 min, and filtered; and the medicine residues are discarded;

step (3), the water extracting solution is concentrated under reduced pressure to a relative density of 1.25-1.30 (82±5° C.), and the ethanol extract is gradually added and the mixture is further concentrated to obtain an extractum;

step (4), the Radix Notoginseng medicinal material is pulverized and sieved by a Pharmacopoeia No. 5 sieve to obtain fine powder;

step (5), the fine powder of Radix Notoginseng is added to the extractum obtained in step (3), and the mixture is mixed uniformly, dried and pulverized to obtain about 1000 mg of the Salvia miltiorrhiza and Radix Notoginseng extract.

3, Salvia miltiorrhiza and Radix Notoginseng granules are prepared according to the following formula:

| | |
|---|---|
| Salvia miltiorrhiza and Radix Notoginseng extract | 1000 mg |
| Borneolum Syntheticum | 30 mg |
| Microcrystalline cellulose | 550 mg |
| Magnesium stearate | 100 mg |

The Salvia miltiorrhiza and Radix Notoginseng extract is mixed with microcrystalline cellulose and Borneolum Syntheticum uniformly, the mixture is added with water to prepare granules, added with magnesium stearate, and mixed uniformly for later use.

4, Ranolazine granules are prepared according to the following formulation:

| | |
|---|---|
| Ranolazine | 500 mg |
| Microcrystalline cellulose | 71 mg |
| Methacrylic acid copolymer type C | 67 mg |
| Sodium hydroxide | 2.7 mg |
| Hypromellose | 14 mg |
| Magnesium stearate | 14 mg |

The ranolazine fine powder is mixed with methacrylic acid copolymer type C, microcrystalline cellulose and hypromellose uniformly. The mixture is added with aqueous sodium hydroxide solution, performed with granulating, drying, and sieving, added with magnesium stearate and mixed uniformly for later use.

5, The Salvia miltiorrhiza and Radix Notoginseng granules and ranolazine granules are compressed into bi-layer tablets to obtain a pharmaceutical composition formulation.

Embodiment 12

1, The pharmaceutical composition of the present invention is composed of Salvia Miltiorrhiza medicinal material 1250 mg, Radix Notoginseng medicinal material 250 mg, Borneolum Syntheticum 15 mg, and ranolazine 250 mg.

2, Salvia miltiorrhiza and Radix Notoginseng extract is prepared as follows:

step (1), the Salvia miltiorrhiza medicinal material is cut to 5 cm or less, the Radix Notoginseng is pulverized into particles with 1 cm or less for later use; an appropriate amount of sodium bicarbonate is weighed (2.25-3% of the amount of medicinal materials) for later use; the weighed Salvia miltiorrhiza, Radix Notoginseng and sodium bicarbonate are put into an extraction tank; 4 times amount of process water is added into each tank, heated and boiled. Keep boiling for about 3 hours, and the mixture is filtered;

step (2), a second extraction is performed on medicinal residues, 5 times the amount of water is added, the mixture is heated and boiled. Keep boiling for about 2 hours, filtered, and the medicinal residues are discarded;

step (3), the extracting solution is concentrated under reduced pressure to a relative density of 1.16-1.20 (80±5° C.) or a corresponding sugar degree of 48-52% to obtain a concentrate; the concentrate is put into an ethanol precipitation tank, an appropriate amount of ethanol is added to adjust the ethanol content to 65-70%, standing for 12-24 hours until the precipitation is complete; the supernatant is separated and the precipitate is discarded; and the supernatant is concentrated and spray-dried to obtain a Salvia miltiorrhiza and Radix Notoginseng extract, and the solid content (the amount of water removed, i.e., the dried weight) thereof is about 150 mg.

3, Salvia miltiorrhiza and Radix Notoginseng fine powder is prepared according to the following formulation:

| | |
|---|---|
| Salvia miltiorrhiza and Radix Notoginseng extract (dried weight) | 150 mg |
| Borneolum Syntheticum | 15 mg |
| Lactose | 60 mg |
| Silicon dioxide | 15 mg |
| Stevioside | 10 mg |
| Magnesium stearate | 10 mg |

The Salvia miltiorrhiza and Radix Notoginseng extract is mixed with Borneolum Syntheticum, stevioside, silicon dioxide, magnesium stearate and lactose, the mixture is pulverized and screened by a 200-mesh sieve to obtain a fine powder of Salvia miltiorrhiza and Radix Notoginseng.

4, Preparation of Ranolazine fine powder:

The ranolazine fine powder is prepared in the following proportions.

| | |
|---|---|
| Ranolazine | 250 mg |
| Lactose | 100 mg |
| Silicon dioxide | 15 mg |
| Stevioside | 10 mg |

Ranolazine is mixed with lactose, silicon dioxide and stevioside uniformly, the mixture is pulverized and screened by a 200-mesh sieve to obtain ranolazine fine powder.

5, After the above-mentioned fine powder of Salvia miltiorrhiza and Radix Notoginseng and ranolazine fine powder are mixed well, they are filled into a plastic powder spray bottle to obtain an inhalant, i.e. a pharmaceutical composition preparation of the present invention.

Embodiment 13

1, The pharmaceutical composition of the present invention is composed of Salvia Miltiorrhiza medicinal material 1250 mg, Radix Notoginseng medicinal material 250 mg, Borneolum Syntheticum 15 mg, and ranolazine 500 mg.

2, Salvia miltiorrhiza and Radix Notoginseng extract is prepared as follows:

step (1), the Salvia miltiorrhiza medicinal material is cut to 5 cm or less, the Radix Notoginseng is pulverized into particles with a diameter of 1 cm or less for later use; the weighed Salvia miltiorrhiza and Radix Notoginseng are put into an extraction tank, 4 times amount of 90% ethanol is added into each tank, and the mixture is heated and boiled. Keep boiling about 90 min±20 min, and filtered;

step (2), water extraction is performed on the medicine residues, 5 times the amount of water is added, the mixture is heated and boiled. Keep boiling at about 60 min±15 min, and filtered; and the medicine residues are discarded;

step (3), the water extracting solution is concentrated under reduced pressure to a relative density of 1.25-1.30 (82±5° C.), and the ethanol extract is gradually added and the mixture is further concentrated to obtain an extractum, namely, a Salvia miltiorrhiza and Radix Notoginseng extract of which the solid content (the amount of water removed, i.e., the dried weight) is about 250 mg.

3, Preparation of capsule contents:

The capsule contents are prepared in the following proportions:

| | |
|---|---|
| Salvia miltiorrhiza and Radix Notoginseng extract (dried weight) | 250 mg |
| Borneolum Syntheticum | 15 mg |
| Ranolazine | 500 mg |
| Hypromellose | 50 mg |
| Soybean oil | 900 mg |
| Beeswax | 30 mg |
| Polysorbate 80 | 5 mg |

The above-mentioned Salvia miltiorrhiza and Radix Notoginseng extract, Borneolum Syntheticum, ranolazine, hypromellose, beeswax and polysorbate 80 are successively added to soybean oil, mixed, homogenized by a colloid mill, and compressed into soft capsules to obtain a pharmaceutical composition preparation of the present invention.

Experimental Example 1 Proportional Screening Experiment of the Pharmaceutical Composition of the Present Invention and its Effect on the Duration of Rotarod Movement in Normal Mice

1 Materials and Methods 1.1 Experimental Animals

CD-1 mice, male, 18-22 g, quality certificate number of experimental animals: 110011200105606931, purchased from Beijing Vital River 1.2 Main Instruments

TABLE 1

Main experimental instruments

| Instrument Name | Instrument Model | Manufacturer | Inspection items |
|---|---|---|---|
| Electronic balance | MS204S | Mettler Toledo Instruments Shanghai Co. Ltd. | Test Article Weighing |
| Balance | T-1000 | Shuangjie Test Instrument Factory, Changshu City | Body weight weighing |
| Analytical balance | ML204 | METTLER TOLEDO | Organ weighing |
| Rotating fatigue tester | ENV-575M | ENV-575M | Exercise endurance test |
| Refrigerator (−80 degrees) | THERMO702 | Haier | Sample storage |

1.3 Pharmaceutical Grouping

The proportion of the pharmaceutical composition of the present application is also obtained by screening, and the present application designs several experimental groups as follows. The Salvia miltiorrhiza and Panax notoginseng extract is prepared according to the method of Embodiment 1:

TABLE 2

| Pharmaceutical composition grouping design | | | | | |
|---|---|---|---|---|---|
| | Salvia miltiorrhiza medicinal material (mg) | Radix Notoginseng medicinal material (mg) | Borneolum Syntheticum (mg) | Ranolazine (mg) | Salvia miltiorrhiza and Radix Notoginseng extract (dried weight) (mg) |
| Composition group 1 | 20000 | 6000 | 180 | 500 | 1300 |
| Composition group 2 | 15000 | 3000 | 120 | 500 | 900 |
| Composition group 3 | 5000 | 1000 | 60 | 500 | 600 |
| Composition group 4 | 3500 | 750 | 20 | 500 | 213 |
| Composition group 5 | 3500 | 750 | 20 | 1000 | 213 |
| Composition group 6 | 3500 | 750 | 20 | 2000 | 213 |

Each of the above pharmaceutical composition groups was converted to a clinically equivalent dose for mice as follows.

TABLE 3

| Conversion of clinically equivalent dose for mice in each pharmaceutical composition group designed according to the present invention | | |
|---|---|---|
| | Traditional Chinese medicine composition (Salvia miltiorrhiza and Radix Notoginseng extract (dried weight) + Borneolum Syntheticum) | Ranolazine |
| Composition group 1 | 303 mg/kg | 102 mg/kg |
| Composition group 2 | 209 mg/kg | 102 mg/kg |
| Composition group 3 | 135 mg/kg | 102 mg/kg |
| Composition group 4 | 48 mg/kg | 102 mg/kg |
| Composition group 5 | 48 mg/kg | 205 mg/kg |
| Composition group 6 | 48 mg/kg | 410 mg/kg |

1.4 Experimental Methods 70 experimental animals were randomly divided into 7 groups (n=10): a normal group, a composition group 1, a composition group 2, a composition group 3, a composition group 4, a composition group 5 and a composition group 6. The mice were administered in advance for 7 days, and the mice in the normal group were administered intragastrically with equivalent distilled water. After the last dose of 60 min, the mice will be placed on the rotarod. With the rotating fatigue tester adjusted to a training state, the mice put on the rotarod were given adaptive training for 10 min, and then the rotating fatigue tester was adjusted to a test state with the rotation speed of 30 r/min. The trained mice were put on the rotarod in turn and continuously observed for 60 min, and we recorded the time that the mice continued to move on the roller without falling off.

2 Experimental Results

In the total experiment, 30 min was used. When the mouse dropped from the rotarod, the channel timer was stopped, and the movement duration and the number of drops of the mouse in 30 min were calculated. The results showed that after 7 days of pre-administration, the exercise duration of mice in the administration groups was improved to different degrees, and the efficacy results were significant and were statistically different from the normal group at the proportion of Salvia miltiorrhiza, Radix Notoginseng, Borneolum Syntheticum and ranolazine being (250-700):(50-150):(3-9):(25-100) in the composition group 3 and the composition group 4.

TABLE 4

| Effect of each composition group on the duration of rotarod movement of normal mice | |
|---|---|
| Groups | Exercise duration (S) |
| Normal group | 1995 ± 441 |
| Composition group 1 | 2347 ± 47 |
| Composition group 2 | 2190 ± 261 |
| Composition group 3 | 2397 ± 30* |
| Composition group 4 | 2386 ± 21* |
| Composition group 5 | 2304 ± 127 |
| Composition group 6 | 2288 ± 248 |

*compared with the normal group, $P < 0.05$

3 Conclusion

Under the experimental conditions, each composition group can improve the duration of rotarod movement of normal mice to different degrees, and the efficacy results were significant at the proportion of Salvia miltiorrhiza, Radix Notoginseng, Borneolum Syntheticum and ranolazine being (250-700):(50-150):(3-9):(25-100) in the composition group 3 and the composition group 4.

Experimental Example 2 Effect of the Pharmaceutical Composition of the Present Invention on Weight-Bearing Swimming Time in Normal Mice 1 Experimental Materials and Methods 1.1 Experimental Animals BALB/c mice, male, 18-22 g, quality certificate number of experimental animals: 1100111911047118

1.2 Pharmaceutical Grouping

Pharmaceutical composition group of the present invention (simply referred to as a composition group): it is prepared according to Embodiment 1. The daily dose converted to mice includes: traditional Chinese medicine composition (Salvia miltiorrhiza and Radix Notoginseng extract (dried weight)+Borneolum Syntheticum) 34 mg/kg and the amount of ranolazine 102 mg/kg;

Control Group:

The traditional Chinese medicine (Salvia miltiorrhiza and Radix Notoginseng extract (dried weight)+Borneolum Syntheticum) is prepared according to the method of Embodiment 1 of the present invention and set to 2 times the dose of the traditional Chinese medicine composition in the pharmaceutical composition of the present invention, namely 68 mg/kg;

In the ranolazine group, it is set as twice the ranolazine dose in the pharmaceutical composition group of the present invention, i.e. about 205 mg/kg;

1.3 Experimental Methods

According to the reference, 40 male mice are randomly divided into 4 groups (n=10): a normal group, a ranolazine group, a traditional Chinese medicine group and a pharmaceutical composition group of the present invention are administered in advance for 7 days, and the mice in the normal group are administered intragastrically with equivalent distilled water. Swimming tests are performed 30 min after the last administration. Mice are fixed a 5% weight of its body weight on the tail, and then placed in a large container filled with water of about 20 cm. Water should not be overfilled, so as to prevent mice from jumping out. The mice are forced to swim to exhaustion until they swim to death, and the time is recorded as the weight-bearing swimming time of the mice. See Table 5 for grouping and dose setting.

TABLE 5

Group setting of weight-bearing swimming endurance study of the pharmaceutical composition of the present invention in normal mice

| Group | traditional Chinese medicine (Salvia miltiorrhiza and Radix Notoginseng extract (dried weight) + Borneolum Syntheticum | Ranolazine |
|---|---|---|
| Normal group | — | — |
| Ranolazine group | — | 205 mg/kg |
| Traditional Chinese medicine group | 68 mg/kg | — |
| Pharmaceutical composition group of the present invention | 34 mg/kg | 102 mg/kg |

2 Experimental Results 2.1 Effect of Weight-Bearing Swimming Endurance on Normal Mice The results show that the traditional Chinese medicine group and the pharmaceutical composition group of the present invention could significantly improve the swimming time of normal mice. The results are shown in Table 6.

TABLE 6

Effect of the pharmaceutical composition of the present invention on weight-bearing swimming endurance in normal mice (x ± s)

| Group | Swimming time (s) |
|---|---|
| Normal group | 3247 ± 1070 |
| Ranolazine group | 3746 ± 1837 |
| Traditional Chinese medicine group | 5843 ± 1562* |
| Composition group | 6666 ± 2612* |

*compared with the normal group, $P < 0.05$

3 Conclusion

Under the experimental conditions, after 7 days of pre-administration, the pharmaceutical composition group of the present invention can significantly prolong the swimming time of normal mice and improve exercise endurance.

Experimental Example 3 Effect of the Pharmaceutical Composition of the Present Invention on Exercise Duration and Cardiac Function in Rats with Myocardial Ischemia

1 Materials and Methods 1.1 Experimental Animals

SD rats, male, 180-220 g, quality certificate number of experimental animals: 110011200109011573.

1.2 Main Instruments

TABLE 7

Main experimental instruments

| Instrument Name | Instrument Model | Manufacturer | Inspection items |
|---|---|---|---|
| Electronic balance | MS204S | Mettler Toledo Instruments Shanghai Co. Ltd. | Test Article Weighing |
| Balance | T-1000 | Shuangjie Test Instrument Factory, Changshu City | Test object weighing |
| Analytical balance | ML204 | METTLER TOLEDO | Organ weighing |
| Refrigerator (−80 degrees) | THERMO702 | Haier | Sample storage |

1.3 Test Object

The pharmaceutical composition group of the present invention is set as two groups in total:

Composition Group 1: it was prepared according to the method of Embodiment 2 of the present invention. The daily doses converted to rats were the traditional Chinese medicine (Salvia miltiorrhiza Radix and Notoginseng extract (calculated by dried weight)+Borneolum Syntheticum) of 50 mg/kg and the amount of ranolazine of 50 mg/kg;

Composition Group 2: it was prepared according to the method of Embodiment 3 of the present invention. The daily doses converted to rats were the traditional Chinese medicine (Salvia miltiorrhiza Radix Notoginseng extract (calculated by dried weight)+Borneolum Syntheticum) of 50 mg/kg and the amount of ranolazine of 25 mg/kg.

Control Group:

The traditional Chinese medicine group (the Salvia miltiorrhiza and Radix Notoginseng extract (dried weight)+Borneolum Syntheticum) was prepared according to the method of Embodiment 2 of the present invention, with the same administration dose as that of the traditional Chinese medicine (Salvia miltiorrhiza and Radix Notoginseng extract (dried weight)+Borneolum Syntheticum) in the composition group, i.e., 50 mg/kg;

The ranolazine group was divided into three groups:

Ranolazine group 1: the dose of ranolazine was set to twice the ranolazine administration dose in the composition group 1, i.e., 100 mg/kg.

Ranolazine group 2: the dose of ranolazine was set to the same of the ranolazine administration dose in the composition group 1, i.e., 50 mg/kg.

Ranolazine group 3: the dose of ranolazine was set to the same of the ranolazine administration dose in the composition group 2, i.e., 25 mg/kg.

2 Experimental Methods 110 experimental animals were purchased, of which 10 animals were set as a sham-operation group, and 100 animals were used for modeling left anterior descending coronary artery ligation. After modeling, surviving rats were randomly divided into a vehicle control group, a traditional Chinese medicine group, a ranolazine group 1, a ranolazine group 2, a ranolazine group 3, a pharmaceutical composition group 1 of the present invention and a pharmaceutical composition group 2 of the present invention according to body weight. After therapeutic administration for 28 days, the rats from the vehicle control group were given the same amount of menstruum by gavage. On the 28th day of intragastric administration, 6 rats in each group were randomly selected for echocardiography. After intragastric administration of 60 min on Day 30, a weight-bearing swimming test was performed, and animal samples were taken after the end of weight-bearing swimming. The groups are shown in Table 8.

TABLE 8

Experimental groups of the study on the protective effect of the pharmaceutical composition of the present invention on rats with myocardial ischemia

| Groups | Traditional Chinese medicine (Salvia miltiorrhiza and Radix Notoginseng extract (dried weight) + Borneolum Syntheticum) | Ranolazine |
|---|---|---|
| Sham-operation group | | |
| Vehicle control group | — | — |
| Traditional Chinese medicine group | 50 mg/kg | — |
| Ranolazine group 1 | | 100 mg/kg |
| Ranolazine group 2 | | 50 mg/kg |
| Ranolazine group 3 | | 25 mg/kg |
| Composition group 1 | 50 mg/kg | 50 mg/kg |
| Composition group 2 | 50 mg/kg | 25 mg/kg |

3 Experimental Results 3.1 Weight-bearing Swimming Duration Test

After intragastric administration of 60 min on Day 30, the experimental animals were subjected to the weight-bearing swimming test. After weighing, the rats, fixed a 5% weight of its body weight on the tail were placed in a transparent container filled with water with an inner diameter of 19 cm and a water depth of 30 cm. The water temperature was 25±2° C. The rats swimming to exhaustion were judged by the standard of losing balance and the head submerged for more than 10 seconds. The time of swimming was recorded as the time of weight-bearing swimming.

TABLE 9

Effect of the pharmaceutical composition of the present invention on weight-bearing swimming duration on rats with myocardial ischemia

| Groups | Weight-bearing swimming duration (s) |
|---|---|
| Vehicle group | 4799 ± 1553 |
| Model group | 823 ± 470# |
| Traditional Chinese medicine group | 2126 ± 1634* |
| Ranolazine group 1 | 1927 ± 1450* |
| Ranolazine group 2 | 1268 ± 513 |
| Ranolazine group 3 | 1108 ± 358 |
| Composition group 1 | 1239 ± 481 |
| Composition group 2 | 1517 ± 629* |

*compared with the model group, $P < 0.05$;
#compared with the vehicle group, $P < 0.05$;

3.2 Echocardiography

After intragastric administration of 60 min on Day 28, 6 rats in each group were randomly selected, and the cardiac function was detected by a portable b-ultrasound instrument. The changes of cardiac ejection fraction (EF) and E/A were detected. The experimental results showed that compared with the vehicle group, the heart EF and E/A of rats in the myocardial ischemia model group were significantly decreased (P<0.05), and the heart EF and E/A of rats in each administration group were improved to varying degrees.

TABLE 10

Effect of the pharmaceutical composition of the present invention on cardiac function in rats with myocardial ischemia

| Groups | Ejection Fraction (EF %) | E/A |
|---|---|---|
| Vehicle group | 66.58 ± 2.83 | 1.25 ± 0.06 |
| Model group | 37.00 ± 2.38# | 0.86 ± 0.16# |
| Traditional Chinese medicine group | 45.63 ± 1.70* | 0.93 ± 0.06* |
| Ranolazine group 1 | 55.32 ± 2.76* | 1.10 ± 0.09* |
| Ranolazine group 2 | 50.52 ± 2.15* | 1.06 ± 0.13* |
| Ranolazine group 3 | 45.03 ± 1.57* | 0.92 ± 0.08 |
| Composition group 1 | 52.02 ± 1.20* | 1.11 ± 0.06* |
| Composition group 2 | 47.23 ± 1.69* | 1.07 ± 0.14* |

*compared with the model group, $P < 0.05$;
#compared with the vehicle group, $P < 0.05$;

3.3 Energy Metabolism Related Enzyme Detection

The experimental results showed that compared with the vehicle group, the enzyme activity of the animal myocardial $Na^+$—$K^+$ATP and $Ca^{2+}$—$Mg^{2+}$-ATP in the model group were significantly decreased, and the activity of these two enzymes in the traditional Chinese medicine group, the ranolazine group and the pharmaceutical composition group of the present invention could be improved in different degrees, and the effect of the pharmaceutical composition group 2 was better.

TABLE 11

Effect of the pharmaceutical composition of the present invention on myocardial $Na^+$—$K^+$-ATP and $Ca^{2+}$—$Mg^{2+}$-ATP activity

| Groups | $Na^+$—$K^+$-ATP (μmol/h/g) | $Ca^{2+}$—$Mg^{2+}$-ATP (μmol/h/g) |
|---|---|---|
| Vehicle group | 55.74 ± 6.82 | 53.66 ± 9.28 |

TABLE 11-continued

Effect of the pharmaceutical composition of the present invention on myocardial $Na^{+}$—$K^{+}$-ATP and $Ca^{2+}$—$Mg^{2+}$-ATP activity

| Groups | $Na^{+}$—$K^{+}$-ATP (μmol/h/g) | $Ca^{2+}$—$Mg^{2+}$-ATP (μmol/h/g) |
|---|---|---|
| Model group | 23.89 ± 7.78# | 18.18 ± 6.41# |
| Traditional Chinese medicine group | 38.52 ± 8.58* | 29.00 ± 5.78* |
| Ranolazine group 1 | 46.04 ± 8.57* | 37.99 ± 8.20* |
| Ranolazine group 2 | 47.10 ± 6.57* | 50.92 ± 6.18* |
| Ranolazine group 3 | 34.98 ± 9.26* | 29.96 ± 7.66* |
| Composition group 1 | 47.09 ± 6.50* | 40.89 ± 8.18* |
| Composition group 2 | 55.28 ± 6.92* | 45.64 ± 7.64* |

*compared with the model group, $P < 0.05$;
#compared with the vehicle group, $P < 0.05$;

3.4 Myocardial Histopathology Detection

Pathological results showed that the myocardium of rats with myocardial ischemia model showed significant fibrosis. The administration of the pharmaceutical composition of the present invention could reduce myocardial fibrosis to varying degrees, causing a certain protective effect on the ischemic myocardium, and the effect of the pharmaceutical composition group 2 of the present invention was better.

TABLE 12

Effect of the pharmaceutical composition of the present invention on the pathogenesis of cardiomyopathy in each group

| Groups | Basically normal (number of cases) | Mild (cardiac muscle fiber partially replaced by collagen fiber) | Severe (decreased myocardial thickness, and occurrence of transmural myocardial infarction) |
|---|---|---|---|
| Normal control | 6 | 0 | 0 |
| Model group | 1 | 1 | 6 |
| Traditional Chinese medicine group | 1 | 2 | 3 |
| Ranolazine group 1 | 4 | 1 | 1 |
| Ranolazine group 2 | 3 | 1 | 2 |
| Ranolazine group 3 | 2 | 2 | 2 |
| Composition group 1 | 2 | 2 | 2 |
| Composition group 2 | 4 | 2 | 0 |

4 Conclusion

Under the experimental conditions, the pharmaceutical composition of the present invention has the effect of improving myocardial fibrosis and cardiac insufficiency caused by myocardial ischemia, and has the effect of improving exercise endurance. Especially, the effect of the pharmaceutical composition group 2 of the present invention is better.

The invention claimed is:

1. A pharmaceutical composition for treating myocardial ischemia, comprising Salvia miltiorrhiza medicinal material in an amount of 250-700 parts by weight, Radix Notoginseng medicinal material in an amount of 50-150 parts by weight, Borneolum Syntheticum in an amount of 3-9 parts by weight, and ranolazine in an amount of 25-100 parts by weight.

2. The pharmaceutical composition according to claim 1, wherein the Salvia miltiorrhiza medicinal material and the Radix Notoginseng medicinal material are obtained by extraction in order to provide Salvia miltiorrhiza and Radix Notoginseng extract, or are obtained by directly pulverizing and mixing to obtain a mixture of Salvia miltiorrhiza and Radix Notoginseng.

3. The pharmaceutical composition according to claim 2, wherein the Salvia miltiorrhiza medicinal material and the Radix Notoginseng medicinal material are obtained by merged extraction as follows: decocting Salvia miltiorrhiza and Radix Notoginseng together with water in an alkaline condition in order to obtain a decocting solution; filtering the decocting solution to provide a filtrate; concentrating the filtrate and precipitating it with alcohol in order to provide a supernatant; filtering the supernatant, and recovering alcohol to obtain an extractum representing the Salvia miltiorrhiza and Radix Notoginseng extract; or, drying the extractum to obtain the Salvia miltiorrhiza and Radix Notoginseng extract.

4. The pharmaceutical composition according to claim 2, wherein the Salvia miltiorrhiza medicinal material and the Radix Notoginseng medicinal material are respectively obtained by water extraction and alcohol precipitation, followed by mixing of the Salvia miltiorrhiza extract and Radix Notoginseng extract to obtain the Salvia miltiorrhiza and Radix Notoginseng extract.

5. The pharmaceutical composition according to claim 2, wherein the Salvia miltiorrhiza medicinal material and the Radix Notoginseng medicinal material are obtained by merged extraction as follows: extracting Salvia miltiorrhiza and Radix Notoginseng with alcohol and then water to provide an extract; filtering the extract to provide a filtrate; and, concentrating the filtrate to obtain an extractum that represents the Salvia miltiorrhiza and Radix Notoginseng extract, or, drying the extractum to provide the Salvia miltiorrhiza and Radix Notoginseng extract.

6. The pharmaceutical composition according to claim 2, wherein the Salvia miltiorrhiza medicinal material is obtained by extraction with ethanol and then water to obtain an extractum, followed by pulverizing the Radix Notoginseng medicinal material and then mixing it with the above extractum in order to obtain the Salvia miltiorrhiza and Radix Notoginseng extract.

7. The pharmaceutical composition according to claim 2, wherein the composition is obtained by: mixing the Salvia miltiorrhiza and Radix Notoginseng extract or mixture with Borneolum Syntheticum and excipients to prepare a first intermediate; mixing the ranolazine and the excipients to obtain a second intermediate; and loading the first and second intermediates, respectively, into different layers.

8. The pharmaceutical composition according to claim 7, wherein the composition comprises a bi-layer tablet, bi-layer drop pill, or bi-layer pellet.

9. The pharmaceutical composition according to claim 2, wherein the composition is obtained by mixing the Salvia miltiorrhiza and Radix Notoginseng extract or mixture with Borneolum Syntheticum and one or more excipients to prepare a first preparation; mixing the ranolazine with one or more excipients to prepare a second preparation; and, combining and packaging the first and second preparations together.

10. The pharmaceutical composition according to claim 9, wherein combining and packaging together comprises mixing and filling the first and second preparations into a suitable container, or, mixing and bagging the first and second preparations and packaging them into a divided-dose package.

11. The pharmaceutical composition according to claim 9, wherein the first and second preparations are respectively a tablet, capsule, granule, drop pill, pill, oral liquid, powder, sublimed preparation, ointment, emulsion, transdermal preparation, or inhalation preparation.

12. A method for preventing or treating myocardial ischemia comprising administering to a subject in need thereof a pharmaceutical composition according to claim 1.

* * * * *